United States Patent [19]

Nakagame et al.

[11] Patent Number: 4,615,885

[45] Date of Patent: Oct. 7, 1986

[54] PHARMACEUTICAL COMPOSITION CONTAINING UROKINASE

[75] Inventors: Fujio Nakagame, Tokyo; Haruo Honda, Kawasaki; Teppei Maruyama, Komae; Noriko Saito, Kawasaki; Tomoaki Kimoto, Matsudo, all of Japan

[73] Assignee: Terumo Kabushiki Kaisha, Tokyo, Japan

[21] Appl. No.: 659,228

[22] Filed: Oct. 9, 1984

[30] Foreign Application Priority Data

Nov. 1, 1983 [JP] Japan ................................. 58-203683
Apr. 11, 1984 [JP] Japan ................................. 59-72384

[51] Int. Cl.$^4$ .............................................. A61K 37/48
[52] U.S. Cl. ..................................................... 424/94
[58] Field of Search ......................................... 424/94

[56] References Cited

U.S. PATENT DOCUMENTS

| | | | |
|---|---|---|---|
| 3,050,445 | 8/1962 | Damaskus et al. | 424/94 |
| 3,072,532 | 1/1963 | Innerfield | 424/94 |
| 3,415,804 | 12/1968 | Polson | 424/94 |
| 3,803,304 | 4/1974 | Antonides | 424/94 |
| 4,258,030 | 3/1981 | Sasaki | 424/94 |

OTHER PUBLICATIONS

Green Cross-Chem. Abst., vol. 96 (1982), pp. 168, 735z.
Tanabe-Chem. Abst., vol. 97 (1982) p. 78900r.

*Primary Examiner*—Sam Rosen
*Attorney, Agent, or Firm*—Frishauf, Holtz, Goodman & Woodward

[57] ABSTRACT

A pharmaceutical composition containing urokinase and a physiological absorption enhancer comprising higher fatty acids, a polyalkylene glycol and calcium is disclosed. Whereas urokinase which is decomposed and inactivated in the stomach and is poorly absorbed from the intestinal tract cannot be orally administered, it can be orally administered in the form of the present composition by applying an enteric coating, because urokinase in the composition is highly absorbable from the intestinal tract. It is desirable in the present composition in view of the stability and sustained absorbability that urokinase is contained in said composition in the form of a liposome preparation in which the urokinase is incorporated in voids of the liposome. The components are incorporated in the present composition at a ratio of 0.01–2 mg. of the higher fatty acid, 0.01–5 mg. of the polyalkylene glycol and 0.0001–0.1 mg. of the calcium per 100 units of urokinase. The present composition is satisfactory for use as a thrombolytic agent.

15 Claims, 4 Drawing Figures

PHARMACEUTICAL COMPOSITION CONTAINING UROKINASE

BACKGROUND OF THE INVENTION

1. Field of the Invention

The present invention relates to a pharmaceutical composition containing urokinase having improved characteristics for intestinal absorption.

More particularly, it is concerned with a pharmaceutical composition containing urokinase improved in intestinal absorbability comprising urokinase and a physiological absorption enhancer.

Urokinase is a fibrinolytic and thrombolytic enzyme. Clinically, it is useful as a thrombolytic agent for a variety of thrombosis such as cerebrovascular obstruction, myocardial infarct and pulmonary embolism. It is also used in combination with antitumor agents.

2. Prior Art

The route of administration of drugs is classified into divisions such as injectable, oral and topical ones. Except for special cases, oral administration is more useful than parenteral in view of the troubles of patient, physician and other persons concerned as well as patients suffering so far as the same result is produced.

When orally administered, urokinase is decomposed and inactivated in the stomach by the actions of such substances as proteases and a gastric acid. Moreover, it is poorly absorbed from the intestinal tract. Heretofore, it has been administered by intravenous injection or by intravenous infusion. Although urokinase can be administered by these routes of administration without decomposition and inactivation, they are unsatisfactory in that each administration has to be exercised by a physician and the patient suffers pain.

In addition, as urokinase has a half life in blood as short as approximately 15 min., maintaining urokinase in blood at a given level is difficult and the effect of the drug is not durable.

SUMMARY OF THE INVENTION

It is an object of the present invention to provide a pharmaceutical composition containing urokinase highly absorbable from the intestinal tract.

Another object of the invention is to provide a pharmaceutical composition containing urokinase improved in intestinal absorbability which is slowly adsorbed and produces durable effects.

In order to achieve the above-mentioned objects the pharmaceutical composition of the invention improved in intestinal absorbability comprises urokinase and a physiological absorption enhancer.

DETAILED DESCRIPTION OF THE INVENTION

Figure 1:
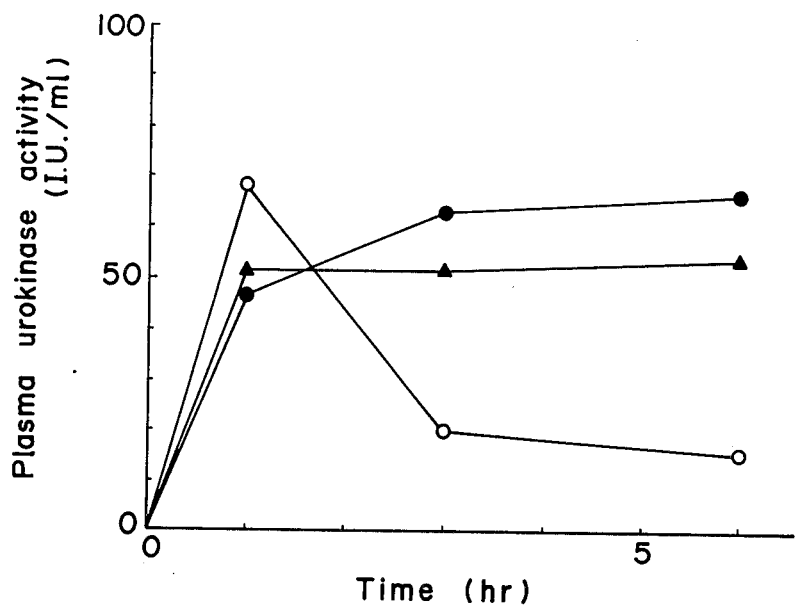
FIG. 1 of the accompanying drawings is a graph indicating the urokinase activity in plasma (I. U./ml.) following gastric administration of enteric coating capsule containing a composition of the invention according to Example 1 or 3 or a control composition.

As described above, urokinase, when orally administered, is decomposed and inactivated in the stomach. Even if the decomposition and inactivation in the stomach is prevented by such a means as an enteric coating, efficiency of the absorption from the intestinal tract is low.

As a result of extensive studies we have found that, unexpectedly, combination of urokinase with higher fatty acids, polyalkylene glycols and calcium results in an efficient absorption of the urokinase from the intestinal tract by oral administration with a high blood level maintained for a long period of time. The present invention is based upon the above finding.

Accordingly, the invention relates to a pharmaceutical composition containing urokinase improved in intestinal absorbability comprisng a therapeutically effective amount of urokinase, and an effective amount of physiological absorption enhancer, said enhancer comprising one or more higher fatty acids, a polyalkylene glycol and calcium.

Any of the urokinases which are pharmaceutically acceptable may be used in the invention. Usually, human-origin urokinases with a molecular weight in the range from 25,000 to 60,000 are employed.

Urokinase contained in the composition of the invention may be in natural form or in the form of an urokinase-carrying liposome preparation in which the urokinase is incorporated into the innerspace of small lipid particles (liposome). When urokinase is contained in the composition of the invention in the form of a liposome preparation, lipids particularly phospholipids suitable for forming liposome are employed as the membrane material for the liposome. As the phospholipid any natural and synthetic phospholipids and hydrogenated derivatives of natural phospholipids may be used. As all of the phospholipids contain unsaturated fatty acids, it is more effective to employ hydrogenated phospholipids in which the unsaturated fatty acids in natural phospholipids are saturated with hydrogen. Synthetic phospholipids may also be employed, but presently they are too expensive to justify economic consideration.

As typical examples of the phospholipid used in the invention are mentioned soybean lecithin, yolk lecithin, corn lecithin, cotton seed oil lecithin, rape lecithin, phosphatidylcholine, phosphatidylethanolamine, phosphatidylinositol, phosphatidylserine, phosphatidylglycerol, sphingomyelin, cardiolipin and the like. In addition, hydrogenated derivatives of these phospholipids prepared by conventional procedures are also mentioned. Especially preferred are hydrogenated derivatives of natural phospholipids from hydrogenation of soybean, yolk, corn, cotton seed oil or rape lecithin. Use of the hydrogenated lecithin enables slower absorption of the urokinase from the intestinal tract with a longer duration of the drug efficacy.

In order to enhance strength of the membrane a sterol such as cholesterol or tocopherol may be added to the membrane material according to the present invention. Sustained release of the drug in the body can be adjusted by the addition of a substance giving negative electric charge such as, for example, phosphatidic acid or dicetylphosphate. Degradation of the liposomal membrane is controlled by the presence of such substance.

The urokinase-carrying liposome preparation of the invention is prepared by a method known per se. For example, a natural phospholipid or a hydrogenated derivative of natural phospholipid and, if desired, a sterol and a substance giving negative electric charge are dissolved in an appropriate solvent such as chloroform or ethanol; an aqueous solution of urokinase is added to the solution; the resulting mixture is vigorously shaken to give a homogeneous dispersion of the aqueous drug solution; and the solvent is distilled off the dispersion to give an urokinase-carrying liposome preparation. The liposome preparation thus obtained is washed with a physiologically acceptable aqueous solution such as physiological saline solution and then formed into pellets, granules or powders.

Lyophilization of the urokinase-carrying liposome preparation of the invention can be carried out under conventional conditions. For example, it is preferably done by freezing the preparation at $-20°$ to $-80°$ C. and subliming the ice under a reduced pressure at or below 0.3 torr. In order to form a good lyophilized cake, a conventional excipient such as mannitol, dextrin or glycin may be added.

Preferable higher fatty acids used in the invention are those which contain 10–20 carbon atoms, examples of which include capric, lauric, myristic, palmitic, stearic, oleic, linolic, linolenic and arachidonic acids. Especially preferred are unsaturated higher fatty acids containing 1–4 double bonds and 18–20 carbon atoms, for example, oleic, linolic, linolenic and arachidonic acids. Oleic acid is most preferable. These higher fatty acids may be used alone or in combination.

As examples of the polyalkylene glycols useful in the invention are mentioned polyethylene glycol and polypropylene glycol. The degree of polymerization of the polyalkylene glycol is preferably in the range between 5 and 500. Polyethylene glycol of a degree of polymerization of 160–200 is especially preferred.

The calcium in the present invention is used in the form of a compound acceptable as a component of pharmaceutical formulations. For example, it is contained in the composition according to the invention in the form of calcium chloride, lactate, phosphate or gluconate.

Part of the above-mentioned higher fatty acid may be contained in the membrane material of liposome in the urokinase-containing liposome preparation of the invention.

By incorporating the higher fatty acid into the membrane structure, the membrane can be changed so as to enlarge voids in the liposome as compared with those in the absence of the higher fatty acid. Moreover, as the higher fatty acid in the membrane is also released when the liposome is degradated, a synergetic absorption-promoting effect is produced in combination with the higher fatty acid separately present in the voids.

The amount of the higher fatty acid incorporated in the membrane is preferably at such a concentration that it is 5% by weight or higher but no micelle of the phospholipid is formed. When the concentration of the higher fatty acid incorporated is 5% by weight or higher, and preferably 10% by weight or higher, there are produced results satisfactory for the objects of the invention in affinity, stability, sustained release and other properties. The concentration should be in such a range that the phospholipid remains in lamella structure. Otherwise, it will not be able to carry the drug in the liposome. Higher concentrations of the higher fatty acid incorporated will result in formation of micelles in which the phospholipid will contain the higher fatty acid at the center with no liposome formed. In such a case, the amount of the higher fatty acid incorporated will reach about 30% by weight, though it is variable depending upon the conditions. Therefore, unless the higher fatty acid is incorporated at a concentration below the one defined above, no liposome will be formed so that the efficiency of carrying the drug will be extremely low or impossible. Preferably, the concentration is 15% by weight or lower. As the amount of the higher fatty acid to be incorporated in the liposome membrane is not sufficient to achieve the objects of the invention, it is desired to add the above-mentioned higher fatty acid as a separate component of the composition.

The ratio of urokinase, higher fatty acids, polyalkylene glycols and calcium to be incorporated in the composition of the invention is from 0.01 to 2 mg., preferably from 0.05 to 0.5 mg. of the higher fatty acids, from 0.01 to 5 mg., preferably from 0.1 to 1 mg. of the polyalkylene glycols and from 0.0001 to 0.1 mg., preferably from 0.0005 to 0.005 mg. of calcium per 100 units of urokinase, although it is not critical.

The composition of the present invention is formulated for oral or rectal administration by conventional procedures. Tablets, capsules or suppositories are prepared by adding as needed, diluents such as calcium carbonate, calcium phosphate, talc, lactose, dextran and starch, binders such as arabic gum and tragacanth powder, lanolin and coconut oil. Since urokinase is decomposed and inactivated with gastric juice, it is desirable to apply an enteric coating to the above-described tablets or capsules by conventional procedures using, for example, hydroxypropylmethylcellulose phthalate.

The content of urokinase per tablet, capsule or suppository is adequately determined in accordance with the dosage of urokinase. For example, urokinase is administered at a daily dose of at least 100,000–500,000 units for the treatment of thrombosis, for which it is desirable to contain 30,000–120,000 units of urokinase per tablet, capsule or suppository.

The present invention will be described below in more details with reference to examples and test examples.

EXAMPLE 1

(1) Preparation of urokinase-carrying liposome powders.

Hydrogenated lecithin, cholesterol and dicetyl phosphate are blended at a molar ratio of 7:7:1. In a 50-ml. egg plant-form flask is placed a solution of 50.6 mg. of the blend in 15 ml. of chloroform. The solvent is distilled off by means of a rotary evaporator to form a thin film on the inner surface of the flask. Then, there is added 6 ml. of 1:1 (volume) mixture of chloroform:isopropylether to dissolve the film, followed by addition of 1 ml. of phosphate buffer (pH 7.2, 0.1M) containing 180,000 units of urokinase. The resulting mixture is subjected to an ultrasonic treatment in a ultrasonic cleaner of water-bath type at 4° C. for 5 min. to a homogeneous dispersion. The solvent is distilled at 40° C. off the dispersion by means of a rotary evaporator until gel is formed. To the gel is added 5 ml. of physiological solution, and the mixture is stirred. Distillation of the solvent is continued for additional 10 min. to give a liposome suspension. The suspension is centrifuged at 100,000 G for 60 min. and washed with two portions of physiological saline solution. The pellets thus obtained are suspended in physiological saline solution and subjected to a sterilization treatment to give an urokinase-carrying liposome. The urokinase-carrying liposome is lyophilized to obtain powdered urokinase-carrying liposome.

(2) Preparation of the composition of the invention.

To a suspension of 35 mg. of oleic acid in an aqueous solution of hardened castor oil are added 100 mg. of polyethylene glycol 6000 and 0.7 mg. of calcium chloride to a solution, which is lyophilized to give powders. The powders are blended with the powdered urokinase-carrying liposome to give a composition of the invention. The composition in admixture with an appropriate amount of polyethylene glycol and dextran are filled in a gelatin capsule to give an urokinase capsule preparation.

EXAMPLE 2

The powdered urokinase-carrying liposome (containing 60,000 units) prepared according to Example 1 (1) is mixed with powders composed of 35 mg. of oleic acid, 100 mg. of polyethylene glycol 6000 and 0.7 mg. of calcium chloride to prepare a composition of the invention. The composition in admixture with an appropriate amount of starch, lactose and arabic gum is tableted and subjected to enteric coating to give urokinase tablets.

EXAMPLE 3

To 10 ml. of an aqueous solution containing 60,000 units of urokinase is added 50 mg. of polyethylene glycol 6000. The mixture is stirred to give a solution, which is lyophilized. The lyophilized mass is blended with powders composed of 35 mg. of oleic acid, 50 mg. of polyethylene glycol 6000 and 0.7 mg. of calcium chloride. The blend in admixture of an appropriate amount of polyethylene glycol and dextran is filled in a gelatin capsule, which is subjected to enteric coating to give a urokinase capsule preparation.

Test Example 1

Absorption Test by Gastric Administration

Wister male rats weighing 200-250 g. were administered into the stomach respectively with an urokinase capsule preparation of the invention prepared according to Example 1 (10,000 units, referred to as Capsule 1 hereinbelow), an urokinase composition of the invention prepared according to Example 3 (10,000 units, referred to as Capsule 2 hereinbelow) and a control capsule preparation of urokinase alone without higher fatty acid, polyalkylene glycol and calcium contained (10,000 units, referred to as Capsule 3 hereinbelow). Blood was drawn from the animals after predetermined periods of time and measured for the blood urokinase level using a synthetic substrate S-2444. Results are graphically shown in FIG. 1.

In FIG. 1, the line with closed circles indicates urokinase activity (I. U./ml.) in plasma when Capsule 1 was administered (average in 10 animals), the line with closed triangles when Capsule 2 was administered (average in 10 animals) and the line with open circles when Capsule 3 was administered (average in 10 animals).

As shown in FIG. 1, the blood level of urokinase was rapidly increased in about 1 hour after administration of Capsule 1 or Capsule 2, and maintained thereafter over 6 hours or longer. On the contrary, the blood level after administration of Capsule 3 was rapidly increased in about 1 hour but was rapidly decreased thereafter with no duration observed.

Test Example 2

Absorption Test by Intraduodenal (referred to as i.d. hereinbelow) Administration Healthy beagle dogs (7-8 months old) weighing 9-13 Kg. were administered by i.d. route respectively with an urokinase capsule preparation of the invention prepared according to Example 1 (30,000 units, referred to as Capsule 4 hereinbelow), an urokinase capsule preparation of the invention prepared according to Example 3 (30,000 units, referred to as Capsule 5 hereinbelow) and a control capsule preparation of urokinase alone without higher fatty acid, polyalkylene glycol and calcium contained (30,000 units, referred to as Capsule 6 hereinbelow). Blood was drawn from the animals after predetermined periods of time and measured for blood $\alpha_2$-PI ($\alpha_2$-plasmin inhibitor) activity using a synthetic substrate S-2251. Results are graphically shown in FIG. 2.

Figure 2:
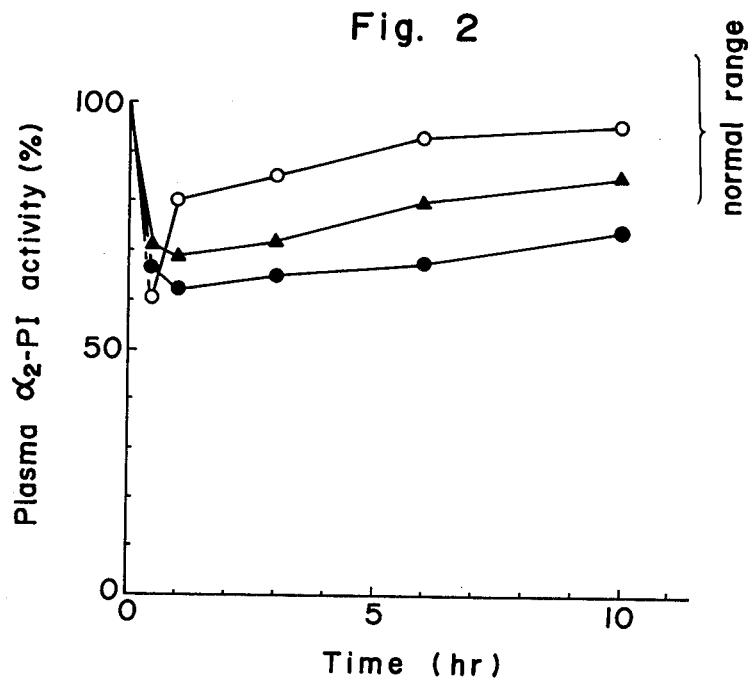
FIG. 2 is a graph indicating $\alpha_2$-PI activity in plasma (%) following gastric administration of enteric coating capsule containing a composition of the invention according to Example 1 or 3 or a control composition.

In FIG. 2, the line with closed circles indicates $\alpha_2$-PI activity (%) in plasma when Capsule 4 was administered (average in 10 animals), the line with closed triangles when Capsule 5 was administered (average in 10 animals) and the line with open circles when Capsule 6 was administered (average in 10 animals).

As shown in FIG. 2, the $\alpha_2$-PI activity was rapidly decreased in about 30 min. after administration of Capsule 4 and maintained thereafter for approximately 10 hours. It was rapidly decreased also with Capsule 5 and maintained for approximately 6 hours. On the contrary, the $\alpha_2$-PI activity after administration of Capsule 6 was rapidly decreased in about 30 min. but returned rapidly to normal level with no duration observed.

As clearly seen from Test Examples 1 and 2 above, the urokinase composition according to the present invention is associated with increase in the efficiency of absorption and duration of the efficacy of the drug as compared with urokinase alone.

EXAMPLE 4

(1) Preparation of a powdered urokinase liposome with a higher fatty acid added.

In 3 ml. of chloroform were dissolved 32 mg. of lecithine, 15.4 mg. of cholesterol and 5 mg. of oleic acid. The solution was placed in a 50-ml. egg plantform flask, to which 3 ml. of isopropylether was added. The mixture was stirred to a blend, to which 1 ml. of an aqueous solution containing 10,000 units of urokinase was added. The resulting mixture was subjected to a sonication at 4° C. for 5 min. in an ultrasonicator of water-bath type to a homogeneous dispersion. The solvent was evaporated by means of a rotary evaporator until gel was formed. The gel was stirred with 5 ml. of physiological saline solution. Evaporation of the solvent was then continued for additional 10 min. to give a liposome suspension. The suspension was centrifuged at 100,000 G for 30 min. and washed with two portions of physiological saline solution. The pellets thus obtained were suspended in physiological saline solution and subjected to a sterilization treatment to give an urokinase liposome. The urokinase liposome was lyophilized to give a powdered urokinase liposome.

(2) Preparation of an absorption enhancer.

To 35 mg. of oleic acid was added 0.5 mg. of HCO-60 (polyoxyethylene-hydrogenated castor oil). The mixture was stirred to a blend, to which was 100 mg. of polyethylene glycol 6000 with 5 ml. of water. The mixture was vigorously stirred to give a homogeneous suspension, to which was then added 0.7 mg. of calcium chloride. After dissolved, the solution was lyophilized to give a powdered absorption enhancer.

(3) Preparation of the composition of the invention (3-1) To a mixture of the powdered urokinase liposome (containing 60,000 units of urokinase and 136 mg. of the powdered absorption enhancer respectively prepared in (1) and (2) above was added an appropriate amount of polyethylene glycol and dextran. The resulting mixture was filled in a gelatin capsule, to which was applied enteric coating.

(3-2) To a mixture of the powdered urokinase liposome (containing 30,000 units of urokinase) and 136 mg. of the powdered absorption enhancer respectively prepared in (1) and (2) above was added an appropriate amount of starch, lactose and hydroxypropylcellulose. The resulting mixture was tableted, and enteric coating was applied to the tablet.

Then, the following tests were run in order to confirm the effect of the urokinase composition improved in enteric absorbability according to the present invention.

Test Example 3

Absorption Test by Gastric Administration

Capsule 7 which was an urokinase-liposome composition of the invention prepared according to Example 4 (3-1) and a lyophilized preparation commercially available were employed.

Wister male rats weighing 200–250 g. were administered each with 10,000 units of urokinase by gastric route for the capsule preparation of the invention or by gastric route or intravenously for the commercial preparation. Blood was drawn at intervals and assayed for the $\alpha_2$-PI ($\alpha_2$-plasmin inhibitor) activity using a synthetic substrate S-2251.

Figure 3:
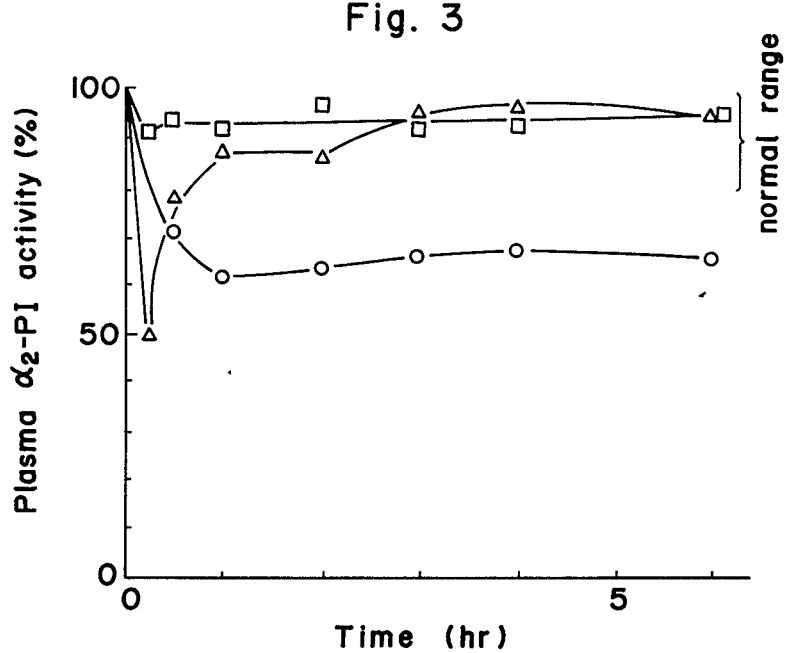
FIG. 3 is a graph indicating changes of $\alpha_2$-PI activity in plasma following gastric or intravenous administration in rats of a composition of the invention according to Example 4 or a control composition.

Results are shown in FIG. 3. The commercial preparation, when administered into the stomach, was absorbed to a very low extent to induce almost no decrease in the $\alpha_2$-PI activity. When administered intravenously, there was observed a rapid decrease in the activity, which was rapidly recovered with no duration observed. On the other hand, administration of Capsule 7 of the invention induced a decrease to approximately 60% after 1 hour, which lasted over 6 hours or longer.

Test Example 4

Absorption Test by Intraduodenal Administration

Capsule 8 which was an urokinase-liposome preparation of the invention prepared according to Example 4 (3-1) and a lyophilized preparation commercially available were employed. Healthy beagle dogs weighing 9–13 Kg. were administered each with 60,000 units of urokinase by duodenal route for the capsule preparation of the invention or by duodenal route or intravenously for the commercial preparation. Blood was drawn at intervals and assayed for the $\alpha_2$-PI ($\alpha_2$-plasmin inhibitor) using a synthetic substrate S-2251.

Figure 4:
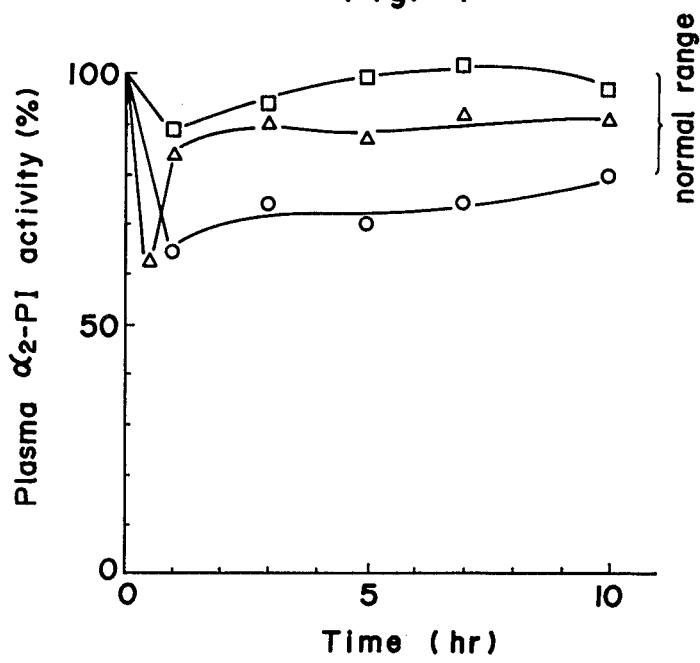
FIG. 4 is a graph indicating changes of $\alpha_2$-PI in plasma following intraduodenal or intravenous administration in dogs of a composition of the invention according to Example 4 or a control composition.

Results are shown in FIG. 4. The commercial preparation, when administered into the duodenum, was absorbed to a very low extent to induce no decrease in the $\alpha_2$-PI activity. When administered intravenously, there was observed a rapid decrease in the activity, which was rapidly recovered with no duration observed. On the other hand, administration of Capsule 8 of the invention induced a decrease to a maximum value of 65% in one hour, which lasted over 10 hours or longer.

In FIGS. 3 and 4, the line with open circles indicates the results with Capsule 7 or 8 of the invention and the lines with open squares indicate the results with the commercial preparation respectively when administered into the stomach (FIG. 3) or the duodenum (FIG. 4). The line with open triangles indicates the results with the commercial preparation when administered intravenously. The results are each an average of the values obtained in 10 animals.

According to the present invention, there is provided an urokinase composition which can be administered by the enteric route. As described above, whereas urokinase alone is absorbed from the intestinal tract only to a very low extent, combination of urokinase with higher fatty acids, polyalkylene glycols and calcium significantly increase the enteric absorption of urokinase. Also according to the invention, an urokinase composition with which the efficacy of urokinase is lasting is provided. Since urokinase is quickly decomposed in blood, it is difficult for the prior-art method of administration to achieve a duration of the efficacy for a long period of time.

On the other hand, the urokinase in the composition of the invention is slowly absorbed from the intestinal tract to enable maintaining a high blood level of urokinase for a long period of time, which in turn enables the efficacy to last. Especially, when urokinase is used in the form of an urokinase-carrying liposome, duration of the efficacy will be longer.

What is claimed is:

1. A pharmaceutical composition containing urokinase comprising a therapeutically effective amount of urokinase and an effective amount of physiological absorption enhancer, said enhancer comprising one or more higher fatty acids, a polyalkylene glycol and a pharmaceutically acceptable calcium.

2. The pharmaceutical composition containing urokinase according to claim 1 wherein the higher fatty acid contains 10–20 carbon atoms.

3. The pharmaceutical composition containing urokinase according to claim 2 wherein the higher fatty acid contains 1–4 double bonds and 18–14 20 carbon atoms.

4. The pharmaceutical composition containing urokinase according to claim 3 wherein the higher fatty acid is oleic acid.

5. The pharmaceutical composition containing urokinase according to claim 3 wherein the polyalkylene glycol is a polyethylene glycol.

6. The pharmaceutical composition containing urokinase as in any one of claims 1–5 wherein the urokinase is an urokinase-carrying liposome preparation.

7. The pharmaceutical composition containing urokinase according to claim 6 wherein the urokinase-carrying liposome preparation is a liposome preparation the membrane material of which contains a lipid and a higher fatty acid.

8. The pharmaceutical composition containing urokinase according to claim 6 wherein the lipid is a hydrogenated lecithin.

9. The pharmaceutical composition containing urokinase according to claim 1 which contains 0.01–2 mg. of the higher fatty acid, 0.01–5 mg. of the polvalkylene glycol and 0.0001-0.1 mg. of the calcium per 100 units of the urokinase.

10. The pharmaceutical composition containing urokinase according to claim 7 wherein the lipid is a hydrogenated lecithin.

11. The pharmaceutical composition containing urokinase according to claim 1 wherein said calcium compound is calcium chloride, calcium lactate, calcium phosphate or calcium gluconate.

12. The pharmaceutical composition containing urokinase according to claim 9 wherein the higher fatty acid contains 1-4 double bonds and 18-20 carbon atoms, the polyalkyleneglycol is a polyetheleneglycol and the urokinase is an urokinase-carrying liposome preparation.

13. The pharmaceutical composition containing urokinase according to claim 12 wherein said higher fatty acid is in an amount of from 0.05 to 0.5 mg, said polyalkyleneglycol is in an amount from 0.1 to 1 mg and said calcium is in an amount from 0.0005 to 0.005 mg per 100 units of urokinase.

14. The pharmaceutical composition containing urokinase according to claim 13 wherein said polyethylene glycol has a degree of polymerization of from 160 to 200 and wherein the urokinase-carrying liposome preparation is a liposome preparation the membrane material of which contains a lipid and a higher fatty acid.

15. The pharmaceutical composition containing urokinase according to claim 14 wherein the higher fatty acid is oleic acid, wherein the lipid is a hydrogenated lecithin and wherein said calcium compound is calcium chloride, calcium lactate, calcium phosphate or calcium gluconate.

* * * * *